United States Patent [19]

Antoun

[11] Patent Number: 5,102,916
[45] Date of Patent: Apr. 7, 1992

[54] METHOD OF RELIEVING GASTRIC ULCERS WITH CAROB EXTRACT

[76] Inventor: Jacques Antoun, 3630 General De Gaulle Dr., New Orleans, La. 70114

[21] Appl. No.: 609,392

[22] Filed: Nov. 5, 1990

Related U.S. Application Data

[63] Continuation-in-part of Ser. No. 547,460, Jul. 3, 1990, abandoned.

[51] Int. Cl.$^5$ ............................................. A61K 35/78
[52] U.S. Cl. ................................... 514/783; 424/195.1
[58] Field of Search ...................... 424/195.1; 514/783

[56] References Cited

U.S. PATENT DOCUMENTS

| | | | |
|---|---|---|---|
| 55,911 | 6/1866 | Salit | 424/195.1 |
| 96,943 | 11/1869 | Miller | 424/195.1 |
| 102,093 | 4/1870 | Cobb | 424/195.1 |
| 118,686 | 9/1871 | Chambers | 424/195.1 |
| 121,631 | 12/1871 | Kennedy | 424/195.1 |
| 177,614 | 5/1876 | Battaglia | 424/195.1 |
| 4,139,612 | 2/1979 | Raudnitz | 424/195.1 |
| 4,937,079 | 5/1990 | Farolfi | 424/195.1 |
| 4,945,084 | 7/1990 | Packman | 424/195.1 |

OTHER PUBLICATIONS

The Dispensatory Wood, 1943, pp. 8517-8518.
Codex Vegetabilis, Steinmetz, 1957, #270, 936.
Encyclopedia of Chemical Technology, vol. 8, Kirk-Othmer, pp. 108-109.
The Merck Index, 1989, #8048, 5436.

Primary Examiner—Ronald W. Griffin
Assistant Examiner—Ralph Gitomer
Attorney, Agent, or Firm—Pravel, Gambrell, Hewitt, Kimball & Krieger

[57] ABSTRACT

A substance for the treatment of ulcers is made from the bark of the cargo tree (*Ceratonia siliqua*) or the encina tree (*Quercus agrifolia*). A solution is made by boiling preferably 250 grams of the bark of either tree in two liters of water for 25 minutes, then straining the solution and letting it cool. 150 milliliters of the cooled solution is taken orally by a sufferer of ulcers preferably three times per day for two or three days.

3 Claims, No Drawings

METHOD OF RELIEVING GASTRIC ULCERS WITH CAROB EXTRACT

This is a CIP of copending application Ser. No. 07/547,460, filed July 3, 1990, now abandoned, and hereby incorporated by reference.

BACKGROUND OF THE INVENTION

1. Field of the Invention

The present invention relates to substances for and methods of relieving gastric ulcers.

2. General Background of the Invention

Gastric ulcers afflict many persons. Until now, there has been no effective relief for many sufferers of gastric ulcers.

SUMMARY OF THE INVENTION

The present invention is a substance which can relieve the suffering of people who have gastric ulcers. The substance of the present invention is made from the bark of the carob tree or the encina tree. A solution is made by boiling preferably 250 grams of the bark of either tree in two liters of water for 25 minutes, then straining the solution and letting it cool. 150 milliliters of the solution is taken orally (drunk) by a sufferer of gastric ulcers preferably three times per day for two or three days.

DETAILED DESCRIPTION OF THE PREFERRED EMBODIMENTS

The substance of the present invention is made from the bark of the carob tree (*Ceratonia siliqua*) or the encina tree (an evergreen oak, *Quercus agrifolia*) (the bark of other similar trees may also work, although no other trees except the two mentioned ones have been found by the inventor to work). A solution is made by boiling preferably 250 grams of the bark of either tree in two liters of water for 25 minutes, then straining the solution and letting it cool. Other proportions of bark to water may be used, but the 250 gram to two liter proportion is preferred. 150 milliliters of the cooled solution is taken orally by a sufferer of gastric ulcers preferably three times per day (preferably at 9:00 a.m., 1:00 p.m., and 6:00 p.m. and preferably at least 15 minutes before eating) for two or three consecutive days. It has been found that by taking the solution described herein gastric ulcers disappear in two or three days. The liquid solution can be stored without harm for several days under refrigeration.

It is also possible to form a dry substance by evaporating the water from the liquid solution or by freeze-drying the liquid solution. The dry substance may advantageously be formed into pills for easy storage and shipment. The pills could then be taken orally on the same schedule as when persons drink the liquid solution. Any suitable base can be used to form the pills, or the pills can be made by placing the powder in capsules.

It is also possible to mix the bark of the carob tree and encina tree in any proportions before mixing with the water. In such a case, it is still preferred to have proportions of 250 grams of bark to two liters of water.

As used herein "gastric ulcer" refers to a necrotic lesion of the stomach or duodenum.

The substance described herein also relieves gastritis, stomach gas and is believed by the inventor to coat the stomach and to relieve ulcers of the mouth. Experiments done by the inventor show that a spoon dipped into the solution when it is hot (and a warm spoon dipped into cold solution) becomes coated with a film.

The foregoing embodiments are presented by way of example only; the scope of the present invention is to be limited only by the following claims.

I claim:

1. A method of treating gastric ulcers in a person in need of treatment consisting essentially of:

orally administering to the person in need of treatment an effective amount of a pharmaceutical composition comprising an extract made from bark from a carob tree (*Ceratonia siliqua*).

2. The method of claim 1 wherein the pharmaceutical composition consists essentially of a solution made by boiling a mixture consisting essentially of bark from a carob tree and water.

3. A method of treating gastric ulcers in a person in need of treatment consisting essentially of:

orally administering to the person in need of treatment an effective amount of a pharmaceutical composition made by boiling a mixture consisting essentially of water and bark from a carob tree (*Ceratonia siliqua*).

* * * * *